(12) United States Patent
Nozawa et al.

(10) Patent No.: US 11,202,562 B2
(45) Date of Patent: Dec. 21, 2021

(54) OPHTHALMIC APPARATUS

(71) Applicant: Tomey Corporation, Nagoya (JP)

(72) Inventors: Yuji Nozawa, Nagoya (JP); Chihiro Kato, Nagoya (JP); Takashi Kamo, Nagoya (JP)

(73) Assignee: Tomey Corporation, Nagoya (JP)

( * ) Notice: Subject to any disclaimer, the term of this patent is extended or adjusted under 35 U.S.C. 154(b) by 221 days.

(21) Appl. No.: 16/562,883

(22) Filed: Sep. 6, 2019

(65) Prior Publication Data

US 2020/0077882 A1 Mar. 12, 2020

(30) Foreign Application Priority Data

Sep. 11, 2018 (JP) .............................. JP2018-169638

(51) Int. Cl.
*A61B 3/00* (2006.01)
*A61B 3/10* (2006.01)
(Continued)

(52) U.S. Cl.
CPC ............ *A61B 3/0025* (2013.01); *A61B 3/102* (2013.01); *B29D 11/00961* (2013.01); *G01B 9/02091* (2013.01); *G02B 27/0031* (2013.01)

(58) Field of Classification Search
CPC . A61B 3/0025; A61B 3/102; B29D 11/00961; G02B 27/0031; G01B 9/02091; G01B 9/02056
(Continued)

(56) References Cited

U.S. PATENT DOCUMENTS 9,192,294 B2 11/2015 Sharma et al.
2009/0261240 A1 10/2009 Watanabe et al.
(Continued)

FOREIGN PATENT DOCUMENTS

EP 2801317 A 11/2014
EP 2949264 A1 12/2015
(Continued)

OTHER PUBLICATIONS

European Search Report ("ESR") for EP App. No. 19196191.1-1122 dated Mar. 13, 2020 (7 pages).

*Primary Examiner* — Mohammed A Hasan
(74) *Attorney, Agent, or Firm* — Shumaker, Loop & Kendrick, LLP (57) ABSTRACT

An ophthalmic apparatus includes: a light source; a measurement optical system that irradiates an eye with light from the source and guides reflected light from the eye; a reference optical system that guides the light from the source to use the light from the source as reference light; an abnormality detection optical system that has an optical path length of a predetermined length and to guide the light from the source to use the light from the source as abnormality detection light; a light receiving element that receives measurement interference light being combination of the reflected light from the eye and the reference light and abnormality detection interference light being combination of the abnormality detection light and the reference light, and the ophthalmic apparatus determines whether the measurement interference light is abnormal based on waveform of an abnormality detection interference signal outputted from the light receiving element.

5 Claims, 7 Drawing Sheets

(51) Int. Cl.
  *B29D 11/00* (2006.01)
  *G01B 9/02* (2006.01)
  *G02B 27/00* (2006.01)

(58) Field of Classification Search
  USPC ........................................................ 351/205
  See application file for complete search history.

(56) References Cited

U.S. PATENT DOCUMENTS

| | | |
|---|---|---|
| 2011/0255054 A1 | 10/2011 | Hacker et al. |
| 2011/0292395 A1* | 12/2011 | Fercher .............. G01B 9/02019 356/451 |
| 2013/0222813 A1 | 8/2013 | Watanabe et al. |
| 2013/0229627 A1 | 9/2013 | Kato et al. |
| 2014/0268057 A1 | 9/2014 | Hacker et al. |
| 2014/0327918 A1 | 11/2014 | Sugiyama et al. |
| 2015/0057958 A1 | 2/2015 | Watanabe et al. |
| 2016/0309997 A1* | 10/2016 | Imamura .............. A61B 3/1241 |
| 2017/0276475 A1* | 9/2017 | Morino .................. G01B 11/24 |
| 2018/0279877 A1* | 10/2018 | Berdahl .................. A61B 3/12 |

FOREIGN PATENT DOCUMENTS

| | | |
|---|---|---|
| JP | 2010-014459 A | 1/2010 |
| JP | 2013-167643 A | 8/2013 |
| JP | 5744752 B2 | 7/2015 |
| JP | 2015-226608 A | 12/2015 |
| JP | 2016-041218 A | 3/2016 |
| JP | 2016-080411 A | 5/2016 |
| JP | 5946654 B2 | 7/2016 |
| JP | 6198448 B2 | 9/2017 |

* cited by examiner

OPHTHALMIC APPARATUS

CROSS-REFERENCE TO RELATED APPLICATION

This application claims priority to Japanese Patent Application No. 2018-169638, filed on Sep. 11, 2018, the entire contents of which are incorporated herein by reference.

TECHNICAL FIELD

The technique disclosed herein relates to an ophthalmic apparatus. To be more precise, it relates to an ophthalmic apparatus configured to measure a subject eye by using light interference.

BACKGROUND

Ophthalmic apparatuses configured to capture tomographic images of inside of a subject eye have been developed. For example, an ophthalmic apparatus of Japanese Patent Application Publication No. 2016-41218 is provided with a measurement optical system configured to irradiate a subject eye with light outputted from a light source and guide reflected light from the subject eye, and a reference optical system configured to irradiate a reference surface with the light outputted from the light source and guide reflected light from the reference surface. In measurement, a tomographic image of the subject eye is generated from an interference light being a combination of the reflected light guided by the measurement optical system and the reflected light guided by the reference optical system.

SUMMARY

When a subject eye is measured using an ophthalmic apparatus such as that described in Japanese Patent Application Publication No. 2016-41218, an abnormality might occur in an interference signal obtained from the interference light. As an example, this may happen when vibration and/or shock cause an abnormality in the interference signal, and/or when a change in current that drives the light source or a change in a temperature of the light source lead to a change in oscillation wavelength (so-called mode hop). It is impossible to measure a subject eye accurately in a situation where such abnormality is occurring. However, there has been a problem that when the interference signal from measurement light that has measured the subject eye wobbles as compared to its normal state, it is difficult to determine what has caused the abnormality, i.e., whether the abnormality is caused due to a capturing state, that is, how the image of the subject eye was captured, or the abnormality is caused due to a presence of a lesion or the like in the subject eye. The present disclosure discloses a technique that determines whether or not there was an abnormality in a capturing state when a subject eye was being measured.

An ophthalmic apparatus disclosed herein may comprise: a light source; a measurement optical system configured to irradiate a subject eye with light from the light source and to guide reflected light from the subject eye; a reference optical system configured to guide the light from the light source so as to use the light from the light source as reference light; an abnormality detection optical system configured to have an optical path length adjusted to a predetermined length and to guide the light from the light source so as to use the light from the light source as abnormality detection light; a light receiving element configured to receive measurement interference light and abnormality detection interference light, the measurement interference light being a combination of the reflected light from the subject eye and the reference light, the abnormality detection interference light being a combination of the abnormality detection light and the reference light; a processor; and a memory storing computer-readable instructions therein, wherein the computer-readable instructions, when executed by the processor, cause the ophthalmic apparatus to execute determining whether the measurement interference light is abnormal based on a waveform of an abnormality detection interference signal, the abnormality detection interference signal being outputted from the light receiving element when the light receiving element receives the abnormality detection interference light.

BRIEF DESCRIPTION OF DRAWINGS

FIGS. 6(*a*), (*b*) show a peak shape of an abnormality detection interference signal, where (a) shows a peak shape in a case where the abnormality detection interference signal is normal, and (b) shows an example of the peak shape in a case where the abnormality detection interference signal is abnormal.

DETAILED DESCRIPTION

Some of the features characteristic to below-described embodiment will herein be listed. It should be noted that the respective technical elements are independent of one another, and are useful solely or in combinations. The combinations thereof are not limited to those described in the claims as originally filed.

An ophthalmic apparatus disclosed herein may comprise: a light source; a measurement optical system configured to irradiate a subject eye with light from the light source and to guide reflected light from the subject eye; a reference optical system configured to guide the light from the light source so as to use the light from the light source as reference light; an abnormality detection optical system configured to have an optical path length adjusted to a predetermined length and to guide the light from the light source so as to use the light from the light source as abnormality detection light; a light receiving element configured to receive measurement interference light and abnormality detection interference light, the measurement interference light being a combination of the reflected light from the subject eye and the reference light, the abnormality detection interference light being a combination of the abnormality detection light and the reference light; a processor; and a memory storing computer-readable instructions therein, wherein the computer-readable instructions, when executed by the processor, cause the ophthalmic apparatus to execute determining whether the measurement interference light is abnormal based on a waveform of an abnormality detection interference signal, the abnormality detection interference signal being outputted from the light receiving element when the light receiving element receives the abnormality detection interference light.

In the above ophthalmic apparatus, by comprising the abnormality detection optical system separately from the measurement optical system, the abnormality detection interference light is generated simultaneously with the measurement interference light when the subject eye is measured. Since the optical path length of the abnormality detection optical system is already known, it is possible to distinguish between a signal generated from the abnormality detection interference light and a signal generated from the measurement interference light. Further, since the abnormality detection interference light is known irrespective of a state of the subject eye, a signal waveform of the abnormality detection interference light can be used to determine whether an abnormality is occurring in the abnormality detection interference light. Because the measurement interference light and the abnormality detection interference light are obtained simultaneously, by detecting the abnormality in the abnormality detection interference light, an abnormality in a capturing state in measurement can be determined, as a result of which an abnormality in the measurement interference light can also be determined.

In an aspect of the ophthalmic apparatus disclosed herein, the light receiving element may be configured to output the abnormality detection interference signal generated from the abnormality detection interference light to the processor, and the computer-readable instructions, when executed by the processor, may cause the ophthalmic apparatus to execute: detecting a position in a depth direction of a peak of the waveform of the outputted abnormality detection interference signal, and determining that the abnormality detection interference light and the measurement interference light received by the light receiving element are abnormal when the detected position is out of a predetermined range, the predetermined range being set based on a position in the depth direction corresponding to the predetermined length. There may be a case where, if an abnormality is occurring in a capturing state while the subject eye is being measured, the position in the depth direction of the abnormality detection interference signal could be displaced. With the above configuration, however, when the abnormality detection interference signal is out of the predetermined range, it is possible to determine the capturing state as being abnormal, and determine that an abnormality is occurring in the received interference light (abnormality detection interference light and measurement interference light).

In an aspect of the ophthalmic apparatus disclosed herein, the light receiving element may be configured to output the abnormality detection interference signal generated from the abnormality detection light to the processor, and the computer-readable instructions, when executed by the processor, may cause the ophthalmic apparatus to execute: detecting a peak shape of the outputted abnormality detection interference signal; and determining that the abnormality detection interference light and the measurement interference light received by the light receiving element are abnormal when the detected peak shape is out of a predetermined range, the predetermined range being set based on a normal peak shape, the normal peak shape being detected at a position corresponding to the predetermined length when no abnormality is occurring. There may be a case where, if an abnormality is occurring in the capturing state while the subject eye is being measured, the peak shape of the abnormality detection interference signal may wobble. With such a configuration, however, when the peak shape of the abnormality detection interference signal is out of the predetermined range, it is possible to determine the capturing state as being abnormal, and determine that an abnormality is occurring in the received interference light (abnormality detection interference light and measurement interference light).

In an aspect of the ophthalmic apparatus disclosed herein, the computer-readable instructions, when executed by the processor, may cause the ophthalmic apparatus to execute: detecting a height of the peak shape of the abnormality detection interference signal; and determining that the abnormality detection interference light and the measurement interference light received by the light receiving element are abnormal when the detected height of the peak shape is out of a predetermined range, the predetermined range being set based on a height of the normal peak shape.

In an aspect of the ophthalmic apparatus disclosed herein, the computer-readable instructions, when executed by the processor, may cause the ophthalmic apparatus to execute detecting a width of the peak shape of the abnormality detection interference signal; an determining that the abnormality detection interference light and the measurement interference light received by the light receiving element are abnormal when the detected width of the peak shape is out of a predetermined range, the predetermined range being set based on a width of the normal peak shape.

Embodiment

Figure 1:
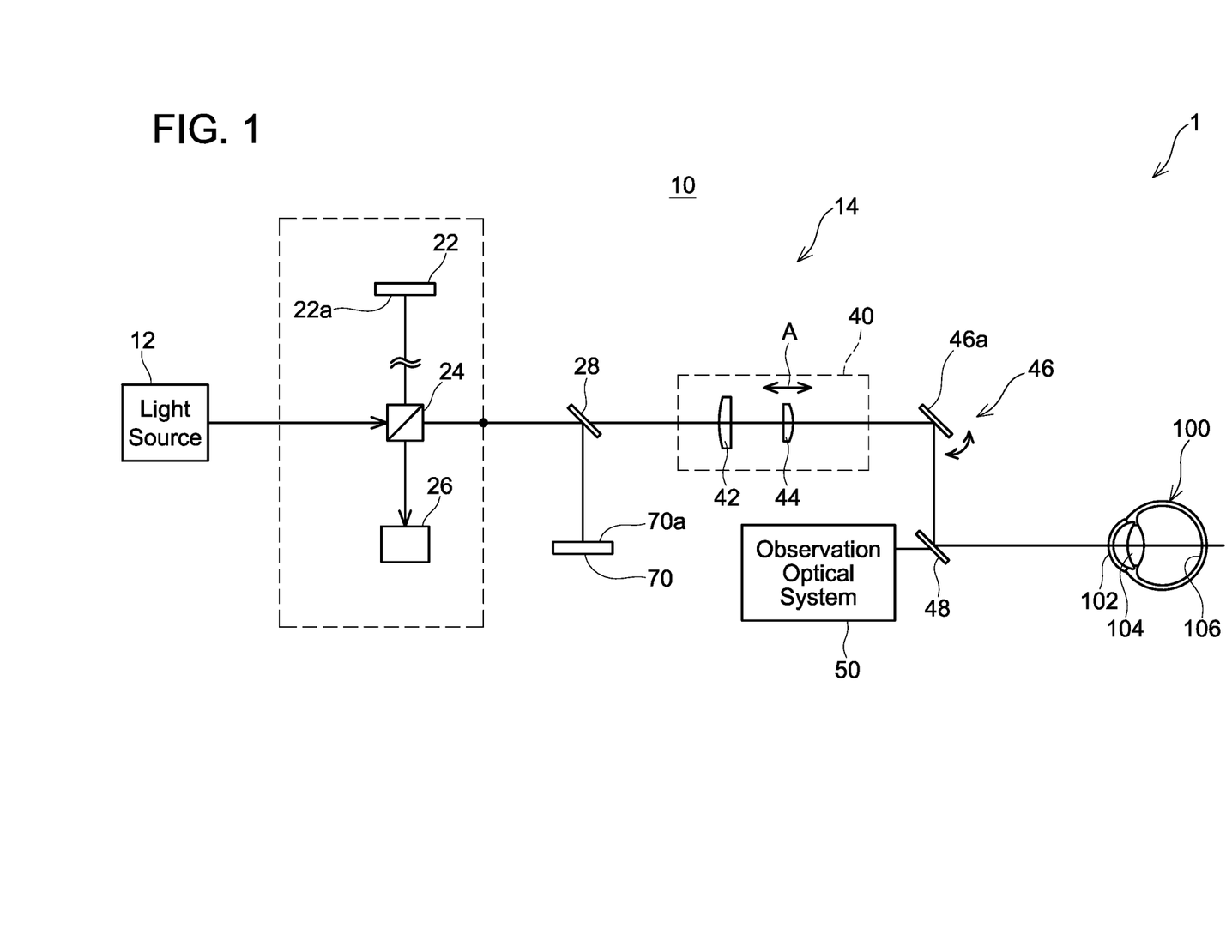
FIG. 1 shows a schematic configuration of an optical system of an ophthalmic apparatus according to an embodiment.

Hereinbelow, an ophthalmic apparatus 1 according to an embodiment will be described. As shown in FIG. 1, the ophthalmic apparatus 1 includes a measurement unit 10 configured to examine a subject eye 100. The measurement unit 10 includes an interference optical system 14 configured to cause reflected light reflected from the subject eye 100 and reference light to interfere with each other, an observation optical system 50 configured to observe an anterior part of the subject eye 100, and an alignment optical system (not shown) configured to align the measurement unit 10 in a predetermined positional relationship with the subject eye 100. Since an alignment optical system used in a known ophthalmic apparatus may be used as the alignment optical system, a detailed description thereof will be omitted.

The interfering optical system 14 is configured of a light source 12, a measurement optical system, a reference optical system, an abnormality detection optical system, and a light receiving element 26. The measurement optical system is an optical system configured to irradiate inside of the subject eye 100 with light from the light source 12 and guide reflected light therefrom. The reference optical system is an optical system configured to irradiate a reference surface 22a with light from the light source 12 and guide reflected light therefrom. The abnormality detection optical system is an optical system configured to irradiate a reflective surface 70a with light from the light source 12 and guide reflected light therefrom. The light receiving element 26 receives measurement interference light being a combination of the reflected light guided by the measurement optical system and the reflected light guided by the reference optical system, and abnormality detection interference light being a combination of the reflected light guided by the abnormality detection optical system and the reflected light guided by the reference optical system.

The light source 12 is a wavelength-sweeping light source, and is configured to change a wavelength of the light emitted therefrom at a predetermined cycle. When the wavelength of the light emitted from the light source 12 changes, a reflected position of reflected light that interferes with the reference light, among reflected light from respective parts of the subject eye 100 in a depth direction, changes in the depth direction of the subject eye 100 in accordance with the wavelength of the emitted light. Due to this, it is possible to specify positions of respective parts (such as a crystalline lens 104 and a retina 106) inside the subject eye 100 by measuring the interference light while changing the wavelength of the emitted light.

The measurement optical system is configured of a beam splitter 24, a beam splitter 28, a focal point adjustment mechanism 40, a Galvano scanner 46, and a hot mirror 48. Light emitted from the light source 12 enters the subject eye 100 through the beam splitter 24, the beam splitter 28, the focal point adjustment mechanism 40, the Galvano scanner 46, and the hot mirror 48. Reflected light from the subject eye 100 is guided to the light receiving element 26 through the hot mirror 48, the Galvano scanner 46, the focal point adjustment mechanism 40, the beam splitter 28, and the beam splitter 24.

The focal point adjustment mechanism 40 is provided with a convex lens 42 disposed on a light source 12 side, a convex lens 44 disposed on a subject eye 100 side, and a second driver 56 (shown in FIG. 2) configured to move the convex lens 44 back and forth with respect to the convex lens 42 in an optical axis direction. The convex lens 42 and the convex lens 44 are disposed on an optical axis and are configured to change a position of a focal point of incident parallel light from the light source 12. When the second driver 56 drives the convex lens 44 in directions of arrow A in FIG. 1, the position of the focal point of the light radiated to the subject eye 100 changes in the depth direction of the subject eye 100, the position of the focal point of the light radiated to the subject eye 100 is adjusted.

The Galvano scanner 46 includes a Galvano mirror 46a, and third driver 58 (shown in FIG. 2) configured to tilt the Galvano mirror 46a. An irradiation position of the measurement light to the subject eye 100 is scanned by the third driver 58 tilting the Galvano mirror 46a.

The reference optical system is configured of the beam splitter 24 and a reference mirror 22. A part of light outputted from the light source 12 is reflected by the beam splitter 24, is directed to the reference surface 22a of the reference mirror 22, and then is reflected by the reference surface 22a of the reference mirror 22. Light reflected by the reference mirror 22 is guided to the light receiving element 26 through the beam splitter 24. The reference mirror 22, the beam splitter 24, and the light receiving element 26 are disposed in an interferometer 20, and their positions are fixed. Therefore, in the ophthalmic apparatus 1 of the present embodiment, a reference optical path length is constant and does not change.

The abnormality detection optical system is configured of the beam splitter 24, the beam splitter 28, and a mirror 70. Light outputted from the light source 12 is reflected by the beam splitter 28 through the beam splitter 24, is directed to the reflective surface 70a of the mirror 70, and is reflected by the reflective surface 70a of the mirror 70. Light reflected by the mirror 70 is guided through the beam splitters 28 and 24 to the light receiving element 26. In the ophthalmic apparatus 1 of the present embodiment, a position of the mirror 70 is fixed. Therefore, an optical path length of the light guided by the abnormality detection optical system (may be referred to as abnormality detection light) is constant and does not change.

Figure 3:
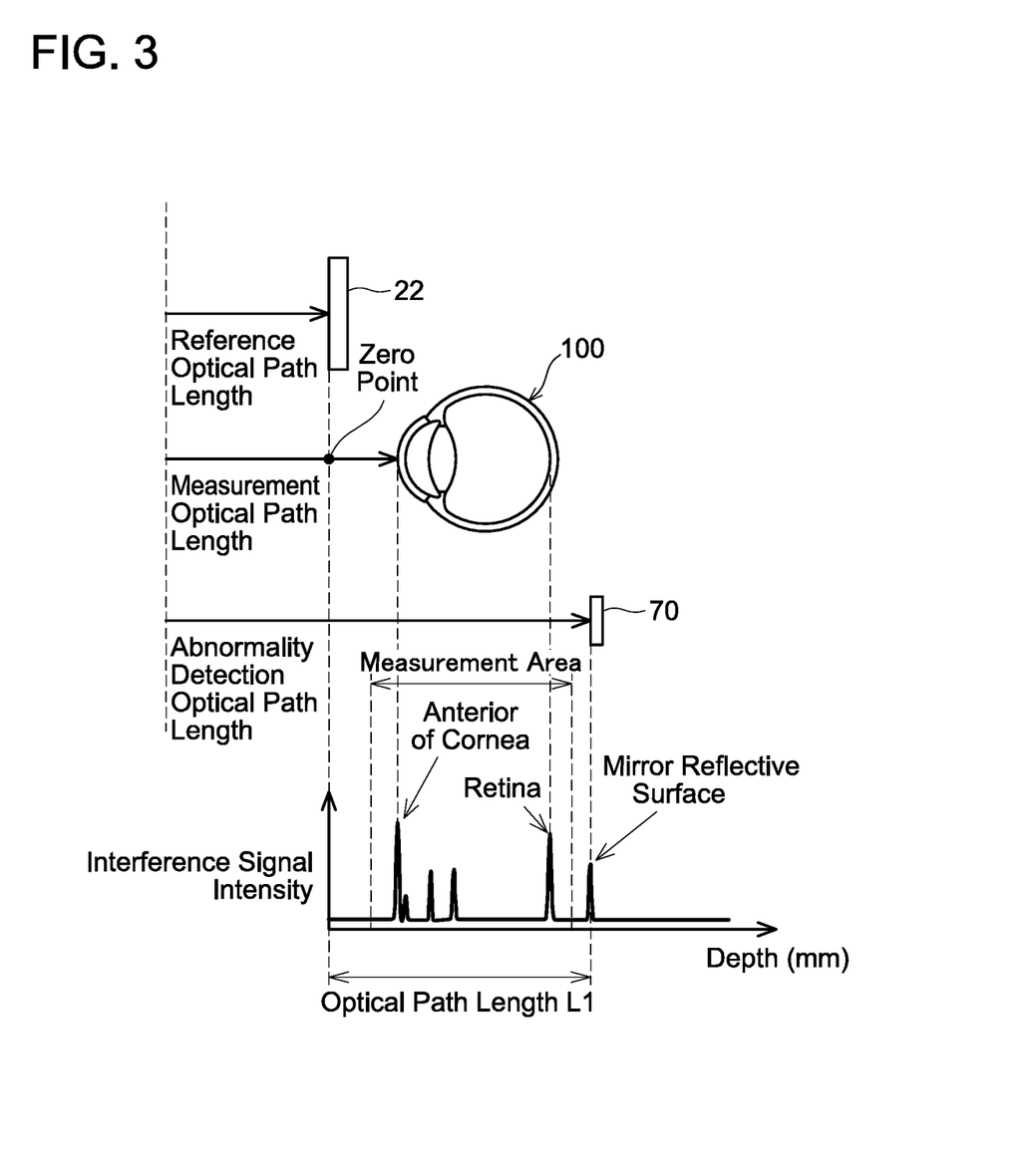
FIG. 3 shows an example of a relation between a zero point, a reference optical path length, a measurement optical path length, and an abnormality detection optical path length.

Further, as shown in FIG. 3, in the abnormality detection optical system, the position of the mirror 70 is set with a zero point as a reference thereof and has been set such that an optical path length L1 from the zero point is longer than a distance from the zero point to the retina 106 of the subject eye 100 when the zero point is set to a position on the light source 12 side than the subject eye 100. The zero point means a point at which an optical path length of the reference optical system (reference optical path length) coincides with an optical path length of the measurement optical system (measurement optical path length). In the present embodiment, the position of the zero point is set to a predetermined position (for example, a position subtly displaced to the light source 12 side from an anterior surface of a cornea 102). By setting the optical path length L1 of the abnormality detection optical system from the zero point to be longer than the distance from the zero point to the retina 106 of the subject eye 100, the reflective surface 70a of the mirror 70 can be detected without overlapping a measurement area of the subject eye 100 (area from the cornea 102 anterior surface to the retina 106). Due to this, a position of the reflective surface 70a can be easily specified.

The light receiving element 26 is configured to detect the measurement interference light being the combination of the light guided by the reference optical system and the light guided by the measurement optical system and the abnormality detection interference light being the combination of the light guided by the reference optical system and the light guided by the abnormality detection optical system. The light receiving element 26 is configured to output interference signals according to the measurement interference light and the abnormality detection interference light when the light receiving element 26 receives the measurement interference light and the abnormality detection interference light. That is, a signal generated from the measurement interference light (measurement interference signal) and a signal generated from the abnormality detection interference light (abnormality detection interference signal) are outputted. These signals are inputted to a processor 64. A photodiode can be implemented for example as the light receiving element 26.

The observation optical system 50 irradiates the subject eye 100 with observation light through the hot mirror 48 and captures reflected light that is reflected from the subject eye 100 (that is, reflected light of the observation light). Here, the hot mirror 48 reflects the light from the light source 12 and transmits light from a light source of the observation optical system 50. As a result, in the ophthalmic apparatus 1 of the present embodiment, it is possible to perform the measurement by the interference optical system 14 and the observation of the anterior part of the eye by the observation optical system 50 at the same time. An observation optical system used in a well-known ophthalmic apparatus can be used as the observation optical system 50. For this reason, detailed configuration thereof is not explained herein.

Further, the ophthalmic apparatus 1 of the present embodiment is provided with a position adjuster 16 (shown in FIG. 2) configured to adjust a position of the measurement unit 10 with respect to the subject eye 100, and a first driver 54 (shown in FIG. 2) configured to drive the position adjuster 16. The position of the measurement unit 10 with respect to the subject eye 100 is adjusted by driving the first driver 54.

Figure 2:
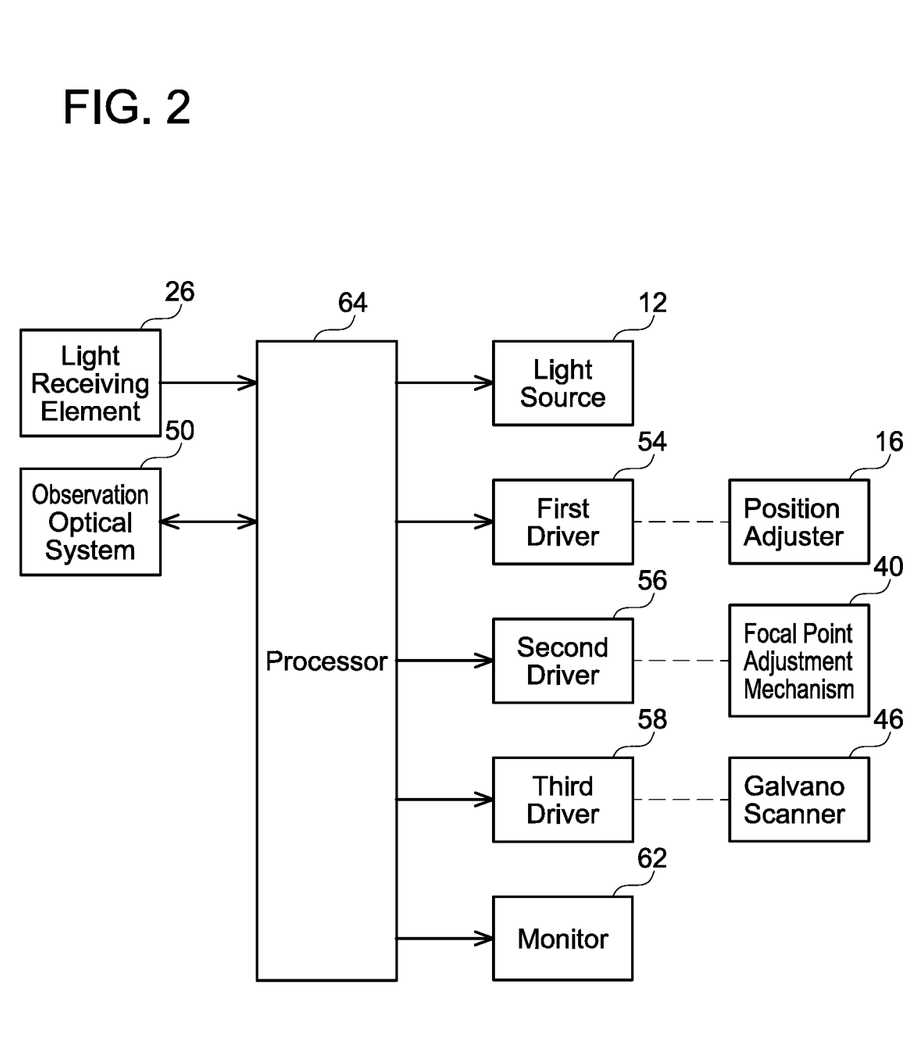
FIG. 2 is a block diagram of a control system of the ophthalmic apparatus according to the embodiment.

Next, a configuration of a control system of the ophthalmic apparatus 1 according to the present embodiment will be described. As shown in FIG. 2, the ophthalmic apparatus 1 is controlled by the processor 64. The processor 64 includes a microcomputer (microprocessor) configured of CPU, ROM, RAM, and the like. The processor 64 is connected to the light source 12, the first to third drivers 54 to 58, a monitor 62, and the observation optical system 50. The processor 64 is configured to control on/off of the light source 12, and drive the position adjuster 16, the focal point adjustment mechanism 40, and the Galvano scanner 46 by controlling the first to third drivers 54 to 58. Further, the processor 64 is configured to control the observation optical system 50 to display an image of the anterior eye part captured by the observation optical system 50 on the monitor 62.

Further, the processor 64 is connected with the light receiving element 26, and interference signals according to intensities of the interference light (i.e., measurement interference light and abnormality detection interference light) detected by the light receiving element 26 are inputted to the processor 64. The processor 64 performs Fourier transform on the interference signals from the light receiving element 26, and specifies positions of respective parts of the subject eye 100 (anterior and posterior surfaces of the cornea 102, anterior and posterior surfaces of the crystalline lens 104, a surface of the retina 106) and of the reflective surface 70a of the mirror 70, and uses these specified positions to calculate an axial length of the subject eye 100.

Subsequently, a process to detect abnormality of a measurement state when the subject eye 100 is measured by using the ophthalmic apparatus 1 according to the embodiment will be described. When the subject eye 100 is measured, an abnormality occurs in the interference signals due to, for example, vibration or shock acting on the ophthalmic apparatus 1, and/or due to a change in oscillation wavelength (so called mode hop) that is caused by a change in current that drives the light source 12 or a change in the temperature of the light source 12. Thus, in a state where these abnormalities are occurring, the subject eye 100 cannot be accurately measured. Therefore, even if a tomographic image is generated using measured data of the subject eye 100 in such a state, the state of the subject eye 100 cannot be correctly grasped. The ophthalmic apparatus 1 according to the present embodiment is configured to detect an abnormality in the aforementioned measurement states and to generate a tomographic image by excluding data measured during when an abnormality is occurring and using only data measured in a normal state. Hereafter, with reference to FIGS. 3-6, the process of detecting an abnormality in the measurement state when the subject eye 100 is being measured will be described.

Figure 4:
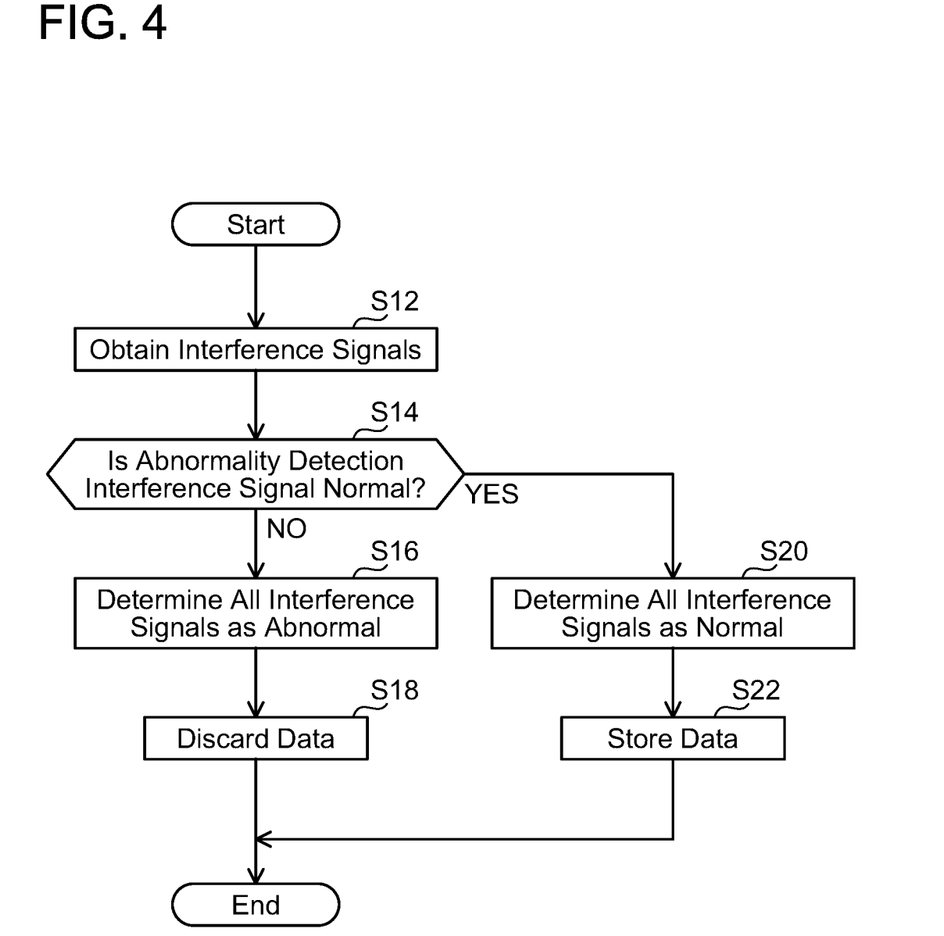
FIG. 4 shows a flowchart showing an example of a process of detecting an abnormality in a measurement state when a subject eye is being measured.

As shown in FIG. 4, firstly, the processor 64 obtains the interference signals (i.e., measurement interference signal and abnormality detection interference signal) (S12). The obtainment of the interference signals is performed by following procedures. Firstly, an examiner operates an operation member, which is not shown, such as a joystick to align the measurement unit 10 with respect to the subject eye 100. That is, the processor 64 drives the position adjuster 16 by the first driver 54 in accordance with the examiner's operation on the operation member. Due to this, a position of the measurement unit 10 in xy-directions (vertical-horizontal directions) and a position thereof in a z-direction (a direction along which the measurement unit 10 moves back and forth) are adjusted with respect to the subject eye 100. Further, the processor 64 drives the second driver 56 to adjust the focal point adjustment mechanism 40. Due to this, a position of the focal point of light irradiated from the light source 12 to the subject eye 100 comes to be positioned at a predetermined position in the subject eye 100 (for example, at the anterior surface of the cornea 102).

Figure 5:
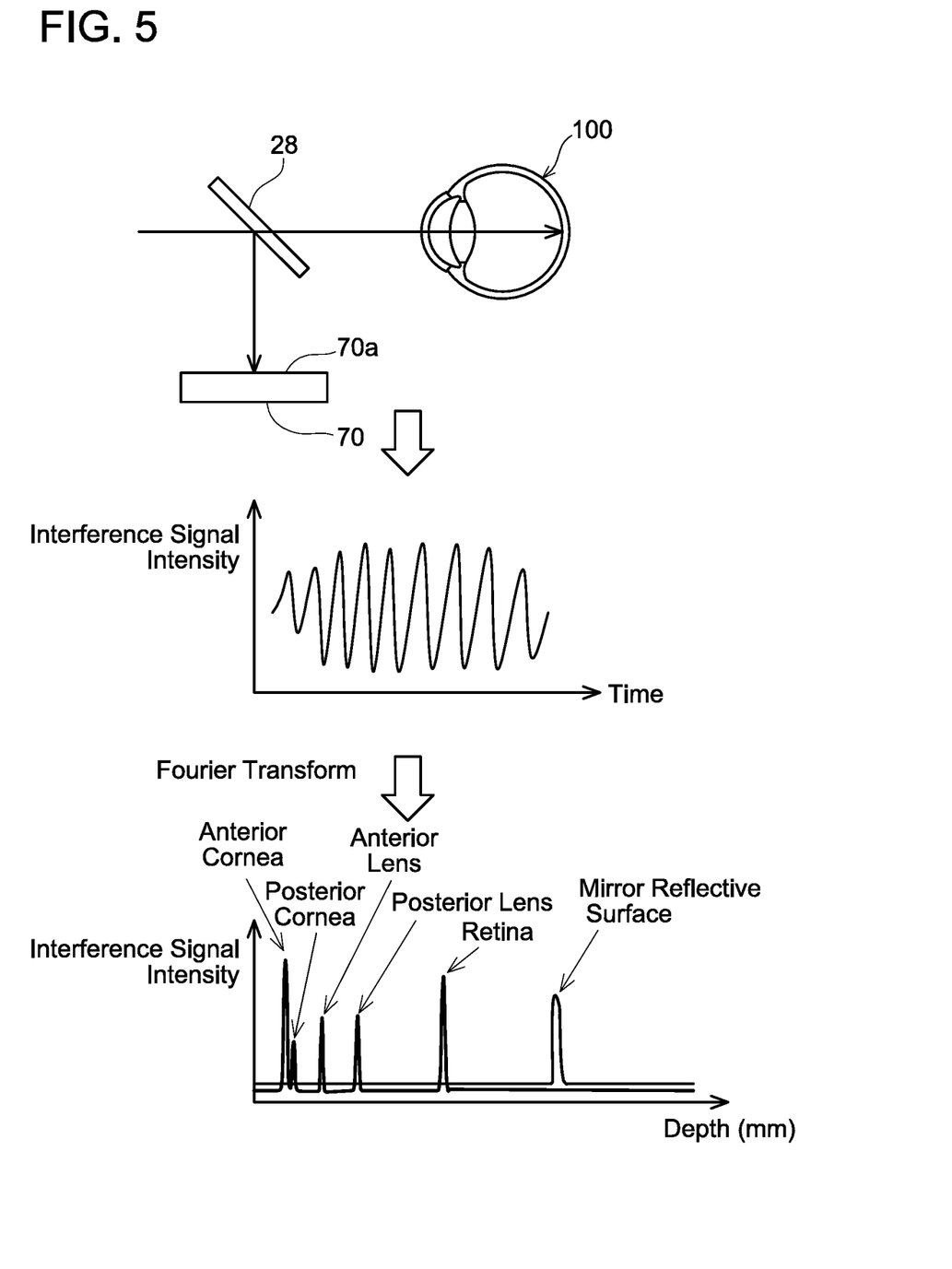
FIG. 5 shows diagrams for explaining a procedure to process an interference signal waveform.
Figure 6:
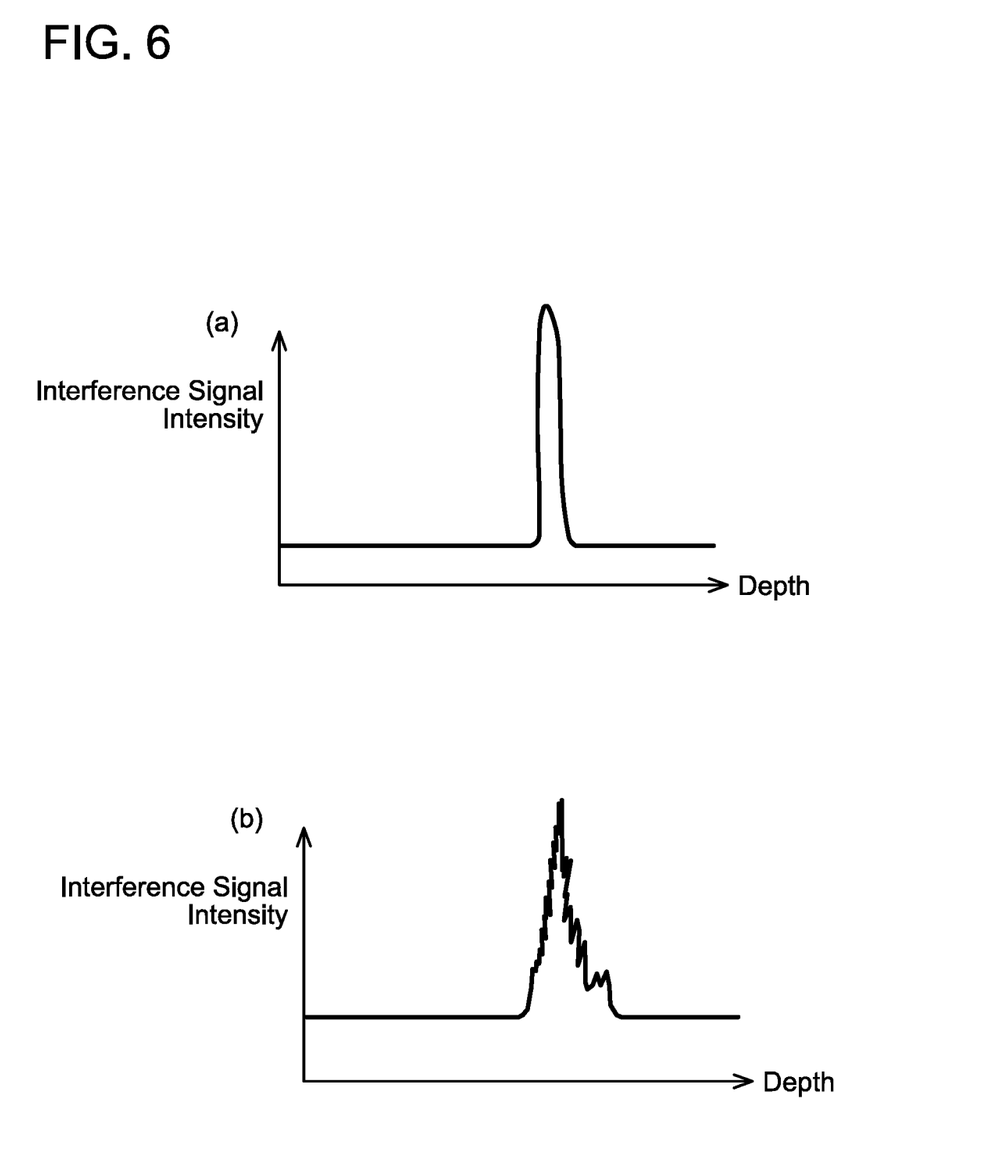

Then, the processor 64 takes in signals detected by the light receiving element 26, while changing the frequency of light from the light source 12. As has already been explained, the interference signals outputted from the light receiving element 26 each becomes a signal of which intensity changes over time as shown in FIG. 5, and these signals include signals generated from an interference wave which is a combination of the reference light and reflected light from the respective parts (the anterior and posterior surfaces of the cornea 102, the anterior and posterior surfaces of the crystalline lens 104, the surface of the retina 106) of the subject eye 100 and an interference wave which is a combination of the reference light and reflected light from the reflective surface 70a of the mirror 70. The processor 64 performs the Fourier transform on the signals inputted from the light receiving element 26 to separate, from those signals, interference signal components respectively generated by the reflected light from the respective parts (the anterior and posterior surfaces of the cornea 102, the anterior and posterior surfaces of the crystalline lens 104, the surface of the retina 106) of the subject eye 100 and from the reflective surface 70a (see graph at bottom of FIG. 5). Due to this, the processor 64 can specify the positions of the respective parts of the subject eye 100 and of the reflective surface 70a.

Upon obtaining the interference signals, the processor 64 determines whether or not the abnormality detection interference signal (i.e., signal by the interference wave which is the combination of the reference light and the reflected light from the reflective surface 70a) is normal (S14). As mentioned above, the optical path length of the abnormality detection light is constant and does not change. Due to this, as shown in FIG. 5, the abnormality detection interference signal after being subjected to the Fourier transform is constantly detected at a certain position in the depth direction. The optical path length L1 from the zero point of the abnormality detection optical system is set to be longer than the distance from the zero point to the retina 106 of the subject eye 100 (see FIG. 3). Due to this, the position of the reflective surface 70a is detected out of the measurement area of the subject eye 100 (more specifically, a position deeper than the measurement area). Accordingly, by performing the Fourier transform on the interference signals which include the measurement interference signal and the abnormality detection interference signal, the abnormality detection interference signal can be specified from among the interference signals. Then, the processor 64 determines whether or not the specified abnormality detection interference signal is normal by determining whether or not the position in the depth direction of and a shape of a waveform (hereafter may be referred to as a peak shape) of the specified abnormality detection interference signal (more specifically, the signal waveform after the Fourier transform, for example, a point spread function signal waveform) are normal.

More specifically, the processor 64 determines that the abnormality detection interference signal is normal in a case where the position in the depth direction of the abnormality detection interference signal is within a predetermined range and also a height and width of the peak in the peak shape of the abnormality detection interference signal are within predetermined ranges (see FIG. 6(a)). On the other hand, the processor 64 determines that the abnormality detection interference signal is abnormal in a case where the position in the depth direction of the abnormality detection interference signal is out of the predetermined range, and/or where at least one of the height and width of the peak in the peak shape of the abnormality detection interference signal are out of the predetermined ranges (see FIG. 6(b)).

Specifically, in the case where the position in the depth direction of the abnormality detection interference signal is out of the predetermined range, regardless of whether or not the peak shape of the abnormality detection interference signal is normal, the abnormality detection interference signal is determined as abnormal. On the other hand, in the case where the position in the depth direction of the abnormality detection interference signal is within the predetermined range, whether or not the abnormality detection interference signal is abnormal is determined based on the peak shape (peak height and width) of the abnormality detection interference signal. For example, even when the peak height of the peak shape of the abnormality detection interference signal is within the predetermined range, in a case where the width of the peak shape is out of the predetermined range, the abnormality detection interference signal is determined as abnormal. Similarly, even when the width of the peak shape of the abnormality detection interference signal is within the predetermined range, in a case where the peak height of the peak shape is out of the predetermined range, the abnormality detection interference signal is determined as abnormal. It should be noted that each of the "predetermined ranges" may not be limited to a particular range, but may be suitably selected.

In the case where the abnormality detection interference signal is determined as not normal (abnormal) (NO in Step S14), the processor 64 determines all the interference signals (i.e., measurement interference signal and abnormality detection interference signal) obtained at step S12 as abnormal (S16). When the ophthalmic apparatus 1 of the present embodiment performs measurement in a normal state, the abnormality detection interference signal after being subjected to the Fourier transform is detected in a known peak shape at a known position in the depth direction. In other words, if the abnormality detection interference signal is not detected normally, it can be determined that the measurement has not been performed in the normal state by the ophthalmic apparatus 1 due to some cause (e.g., vibration or shock, mode hop). When an abnormality occurs in the measurement as above, it can be determined that, not only the abnormality detection interference signal but also the measurement interference signal obtained simultaneously therewith has not been measured normally. Accordingly, the processor 64 determines that the measurement interference signal is also abnormal when the abnormality detection interference signal is determined as abnormal (NO in Step S14). Then, the processor 64 discards data of all the interference signals (measurement interference signal and abnormality detection interference signal) that have been determined as abnormal (S18).

On the other hand, in the case where the abnormality detection interference signal is determined as normal (YES in step S14), the processor 64 determines that all the interference signals (i.e., measurement interference signal and abnormality detection interference signal) obtained in step S12 have been measured normally (S20). That is, because the abnormality detection interference signal after being subjected to the Fourier transform is detected normally, the signal is determined as having been measured in the normal state. Due to this, the measurement interference signal obtained simultaneously with the abnormality detection interference signal is also determined as having been measured in the normal state. Then, the processor 64 stores data of all the interference signals (measurement interference signal and abnormality detection interference signal) in a memory (not shown) (S22).

The above processing is performed for each scan angle. As a result of this, since the data measured in the state where an abnormality is occurring is discarded, a tomographic image constituted of only the data measured in the normal state can be generated. When the data measured in the abnormal state is included in the tomographic image, the tomographic image will include a distortion. Such distortion makes it difficult to evaluate the state of the subject eye 100 correctly. By generating the tomographic image with the data measured in the abnormal state excluded such that a distortion caused by the abnormality in the measurement state can be excluded, the state of the subject eye 100 can be correctly evaluated.

Figure 7:
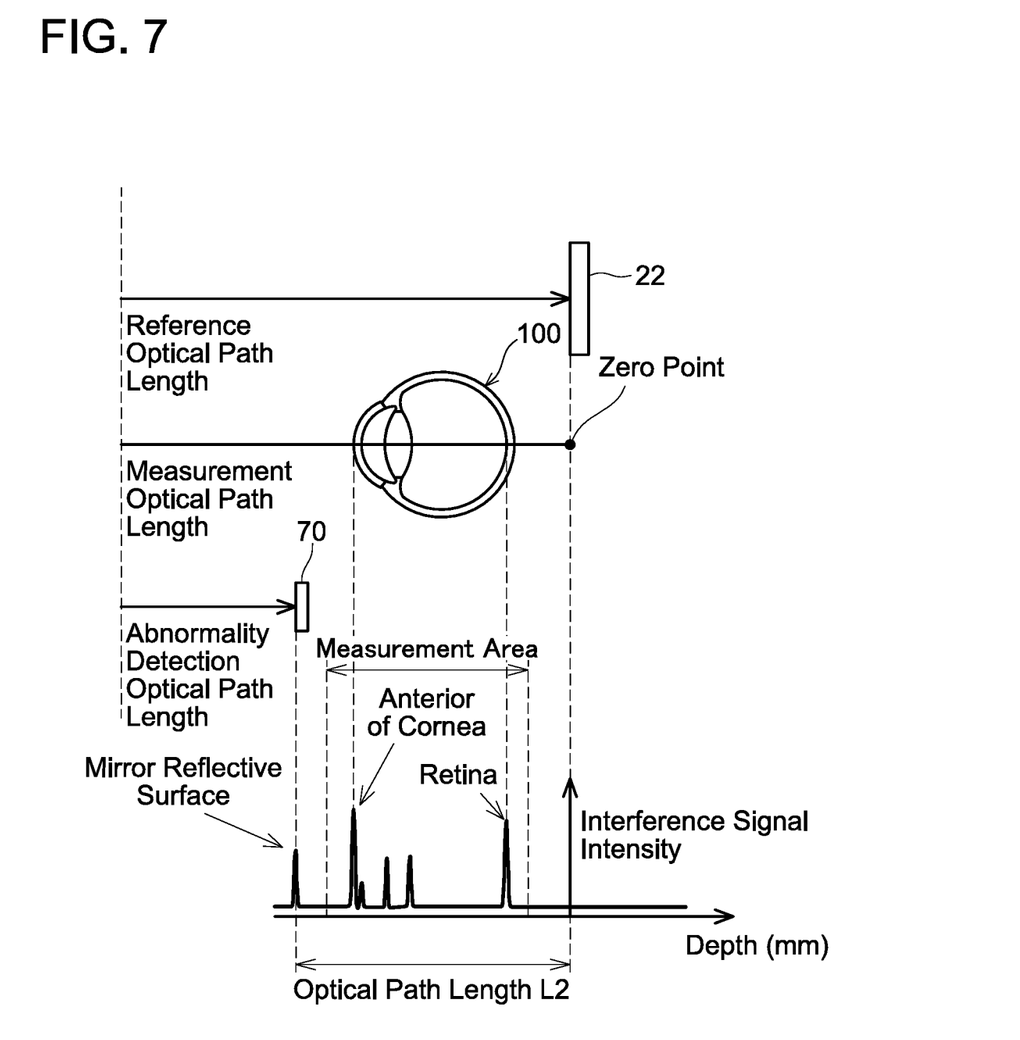
FIG. 7 shows another example of the relation between the zero point, the reference optical path length, the measurement optical path length, and the abnormality detection optical path length.

Although in the present embodiment the zero point is set to the position on the light source 12 side than the subject eye 100, and the optical path length L1 from the zero point of the abnormality detection optical system is set to be longer than the distance from the zero point to the retina 106 of the subject eye 100, such configuration is non-limiting. The position of the reflective surface 70a only needs to be configured so as to be detected out of the measurement area of the subject eye 100, for example, the optical path length from the zero point of the abnormality detection optical system may be set to be shorter than a distance from the zero point to the cornea 102 of the subject eye 100. The zero point may be set to a position away from the light source 12 relative to the subject eye 100 and an optical path length L2 from the zero point of the abnormality detection optical system may be set to be longer than the distance from the zero point to the cornea 102 of the subject eye 100 (see FIG. 7), and may be set to be shorter than the distance from the zero point to the retina 106 of the subject eye 100. Further, the optical path length of the abnormality detection optical system may be longer than a distance from the light source 12 to the zero point, and may be set to a position at which the optical path length of the abnormality detection optical system becomes shorter than the distance from the light source 12 to the zero point. For example, the optical path length of the abnormality detection optical system may be longer by the optical path length L1 from the zero point (at a position shown in FIG. 3), and set to be shorter by the same optical path length L1 from the zero point. In either case, since the distance from the zero point is the same, the abnormality detection interference signal can be detected in the same position in the obtained data.

In the present embodiment, the positions of the zero point and the mirror 70 are fixed at predetermined positions, but such configuration is non-limiting. The position of the reflective surface 70a needs only to be detected out of the measurement area of the subject eye 100, and for example the position of the zero point may be configured to be adjustable, and also the position of the mirror 70 may be configured to be adjustable. In such a case, by adjusting the position of the mirror 70 with the zero point as a reference after adjusting the position of the zero point and setting the optical path length from the zero point of the abnormality detection optical system to be a predetermined length as aforementioned, the position of the reflective surface 70*a* can be easily specified.

In the ophthalmic apparatus 1 of the present embodiment, the abnormality detection optical system is provided with the mirror 70, but such configuration is non-limiting. The optical path length of the abnormality detection optical system only needs to be configured to guide known abnormality detection light, for example, the optical path length of the abnormality detection optical system may be configured to guide the known abnormality detection light by using optical fiber a fiber length of which is adjusted to be a predetermined length in advance. Further, in the abnormality detection optical system, a scatterer may be provided instead of the mirror 70. By providing the scatterer in the abnormality detection optical system, axis displacement of the abnormality detection light can be suppressed.

In the present embodiment, whether or not the obtained interference signal(s) are normal is determined, and the data determined as abnormal is discarded, but such configuration is non-limiting. For example, the processor 64 may determine whether an interference signal at each scan angle is normal or not on one-by-one basis after having obtained (stored) all the interference signals at relevant scan angles. In this case, the processor 64 may not discard the data determined as abnormal, and may generate a tomographic image by selecting the data determined as normal without using the data determined as abnormal.

Further, in the present embodiment the processor 64 which the ophthalmic apparatus 1 comprises is configured to perform the abnormality detection process as described above, but such configuration is non-limiting. For example, data of the interference signals obtained by the ophthalmic apparatus 1 of the present embodiment may be inputted to an external processor which performs the abnormality detection process so as to generate a tomographic image.

Further, the ophthalmic apparatus 1 of the present embodiment is an ophthalmic apparatus of Fourier domain type (SS-OCT type) comprising the wavelength-sweeping light source 12, but such configuration is non-limiting. For example, the ophthalmic apparatus may be of Spectral domain type (SD-OCT type) or may be of Time domain type (TD-OCT type).

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. An ophthalmic apparatus comprising:
a light source;
a measurement optical system configured to irradiate a subject eye with light from the light source and to guide reflected light from the subject eye;
a reference optical system configured to guide the light from the light source so as to use the light from the light source as reference light;
an abnormality detection optical system configured to have an optical path length from the light source adjusted to a predetermined length and to guide the light from the light source so as to use the light from the light source as abnormality detection light; a light receiving element configured to receive measurement interference light and abnormality detection interference light, the measurement interference light being a combination of the reflected light from the subject eye and the reference light, the abnormality detection interference light being a combination of the abnormality detection light and the reference light;
a processor; and
a memory storing computer-readable instructions therein, wherein the computer-readable instructions, when executed by the processor, cause the ophthalmic apparatus to execute:
determining that the abnormality detection interference light is abnormal when at least one of a position of a waveform in a depth direction and a shape of the waveform of an abnormality detection interference signal is out of a predetermined range, the abnormality detection interference signal being outputted from the light receiving element when the light receiving element receives the abnormality detection interference light; and
determining that the measurement interference light is abnormal when it is determined that the abnormality detection interference light is abnormal.

2. The ophthalmic apparatus according to claim 1, wherein
the light receiving element is configured to output the abnormality detection interference signal generated from the abnormality detection interference light to the processor, and
the computer-readable instructions, when executed by the processor, cause the ophthalmic apparatus to execute:
detecting a position in a depth direction of a peak of the waveform of the outputted abnormality detection interference signal, and
determining that the abnormality detection interference light and the measurement interference light received by the light receiving element are abnormal when the detected position is out of a predetermined range, the predetermined range being set based on a position in the depth direction corresponding to the predetermined length.

3. The ophthalmic apparatus according to claim 1, wherein
the light receiving element is configured to output the abnormality detection interference signal generated from the abnormality detection light to the processor, and
the computer-readable instructions, when executed by the processor, cause the ophthalmic apparatus to execute:
detecting a peak shape of the outputted abnormality detection interference signal; and
determining that the abnormality detection interference light and the measurement interference light received by the light receiving element are abnormal when the detected peak shape is out of a predetermined range, the predetermined range being set based on a normal peak shape, the normal peak shape being detected at a position corresponding to the predetermined length when no abnormality is occurring.

4. The ophthalmic apparatus according to claim 3, wherein
the computer-readable instructions, when executed by the processor, cause the ophthalmic apparatus to execute:
detecting a height of the peak shape of the abnormality detection interference signal; and
determining that the abnormality detection interference light and the measurement interference light received by the light receiving element are abnormal when the detected height of the peak shape is out of a predetermined range, the predetermined range being set based on a height of the normal peak shape.

5. The ophthalmic apparatus according to claim 3, wherein
the computer-readable instructions, when executed by the processor, cause the ophthalmic apparatus to execute:
detecting a width of the peak shape of the abnormality detection interference signal; and
determining that the abnormality detection interference light and the measurement interference light received by the light receiving element are abnormal when the detected width of the peak shape is out of a predetermined range, the predetermined range being set based on a width of the normal peak shape.

* * * * *